(12) United States Patent
Ratna et al.

(10) Patent No.: US 6,294,109 B1
(45) Date of Patent: *Sep. 25, 2001

(54) FERROELECTRIC AND ELECTROCLINIC LIQUID CRYSTAL MATERIALS WITH SUB-AMBIENT TEMPERATURE STABILITY, BROAD OPERATION RANGE, AND FAST DYNAMIC RESPONSE

(75) Inventors: Banahalli R. Ratna; Ranganathan Shashidhar, both of Springfield; Jawad Naciri, Falls Church, all of VA (US); Gregory P. Crawford, Palo Alto, CA (US); Joel M. Schnur, Burke, VA (US)

(73) Assignee: The United States of America as represented by the Secretary of the Navy, Washington, DC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/489,920

(22) Filed: Jun. 13, 1995

(51) Int. Cl.$^7$ .......................... C09K 19/20; C09K 19/12; C07C 69/76; C07C 25/13
(52) U.S. Cl. .............................. 252/299.65; 252/299.64; 252/299.67; 560/43; 560/48; 560/84; 570/129
(58) Field of Search ............... 252/299.01, 299.64, 252/299.65, 299.66, 299.67; 570/129; 560/43, 48, 84

(56) References Cited

U.S. PATENT DOCUMENTS

| | | | |
|---|---|---|---|
| 4,729,847 | 3/1988 | Miyazawa et al. | 252/299.64 |
| 4,927,244 | 5/1990 | Bahr et al. | 350/350 S |
| 4,966,727 | 10/1990 | Ichihashi et al. | 252/299.61 |
| 5,013,476 | 5/1991 | Boller et al. | 252/299.61 |
| 5,116,527 | 5/1992 | Coates et al. | 252/299.61 |
| 5,168,381 | 12/1992 | Walba | 359/53 |
| 5,262,086 | 11/1993 | Suzuki et al. | 252/299.65 |
| 5,277,838 | 1/1994 | Haas et al. | 252/299.01 |
| 5,374,376 | 12/1994 | Higashii et al. | 252/299.65 |
| 5,380,915 | 1/1995 | Morita et al. | 560/59 |
| 5,543,078 | * 8/1996 | Walba et al. | 252/299.65 |

FOREIGN PATENT DOCUMENTS

| | | |
|---|---|---|
| 9111025 | 12/1991 | (GB) . |
| 92/20058 | * 11/1992 | (WO) . |

* cited by examiner

Primary Examiner—Shean C. Wu
(74) Attorney, Agent, or Firm—John J. Karasek; Jane B. Marciniszyn

(57) ABSTRACT

A new class of mesogenic compounds has the formula:

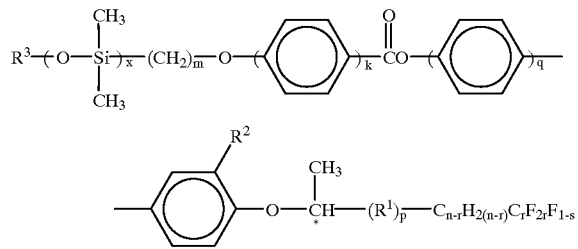

where $R^1$ is an ester (—COO—) group; $R^2$ is H, $NO_2$, CN, F, or Cl; $R^3$ is H, $CH_2$=CH, or $(CH_3)_3Si$; k is 1 or 2; q is 0 or 1; m is from 2 to 16; n is from 2 to 12; r is from 0 to n−1 (but not greater than 3 or 4); s=1 when r=0, s=0 when r≠0; x is from 0 to 4; and * denotes the position of a chiral carbon. Compounds within this class will have a smectic A* phase, and in some cases a smectic C* phase. Mixtures including one or more of these mesogenic compounds will be useful for a variety of applications.

13 Claims, 15 Drawing Sheets

FERROELECTRIC AND ELECTROCLINIC LIQUID CRYSTAL MATERIALS WITH SUB-AMBIENT TEMPERATURE STABILITY, BROAD OPERATION RANGE, AND FAST DYNAMIC RESPONSE

BACKGROUND OF THE INVENTION

1. Field of the Invention

The present invention relates to mesogenic materials, and more particularly to a new class of mesogenic materials having smectic C* and smectic A* phases and exhibiting ferro-electric and electroclinic properties. The invention also relates to mixtures of these compounds.

2. Description of the Related Art

Liquid crystals used in display devices typically are ferroelectric liquid crystals or electroclinic liquid crystals. Typically, a mixture of several mesogenic (i.e., possessing at least one liquid crystal phase) materials are used in a given device. By carefully selecting components and ratios in a mixture of liquid crystals, optimized properties may be obtained that could not be achieved with a single liquid crystal.

A. Ferroelectric Liquid Crystals

Ferroelectric liquid crystal materials (FLC) have a permanent electric polarization in the absence of an applied electric field (analogous to the permanent magnetic polarization of ferromagnetic materials in the absence of an applied magnetic field). These ferroelectric materials are useful for display devices. In particular, these materials are useful for surface-stabilized ferroelectric liquid crystal (SSFLC) display devices.

Desirable properties for a FLC, or for a mixture of FLCs in an SSFLC device include: (1) displaying the ferroelectric smectic C* phase over a broad range of temperatures, (2) possessing a low melting temperature so the ferroclectric phase is stable to sub-ambient temperatures (i.e., below about 25° C.), (3) possessing a large tilt angle (>20°), and (4) having a fast electro-optical response time so that framing rates of 1 kHz or more are achievable.

Existing FLCs are unsatisfactory to one degree or another.

B. Electroclinic Liquid Crystals

In the presence of an applied electric field parallel to the smectic planes, molecules of an electroclinic liquid crystal will tilt with respect to the plane of this applied electric field. The magnitude of the tilt is proportional to the of the applied field. The proportionality constant is generally referred to as the electroclinic coefficient, and is represented as $d\theta/dE$. Because of this proportionality between field and tilt angle, electroclinic materials provide a gray-scale capability that ferroelectric materials do not provide.

These electroclinic materials are also useful for a range of applications, including optical and image processing, optical correlators and interconnects, real time holography, and neural network circuit elements. Desirable properties for an electroclinic liquid crystal, or for a mixture of electrocilnic liquid crystals in a device include: (1) displaying the electroclinic smectic A* phase over a broad range of temperatures, (2) possessing a low melting temperature so the electroclinic phase is stable to sub-ambient temperatures (i.e., below about 25° C.), (3) possessing a large induced tilt angle (>20°) for maximum contrast, (4) having this large induced tilt angle over a broad temperature range, and (5) having a fast electro-optical response time so that framing rates of 1 kHz or more are achievable.

Existing electroclinic liquid crystals are unsatisfactory to one degree or another. See U.S. Pat. No. 5,168,381, issued Dec. 1, 1992 to Walba, U.S. Pat. No. 5,116,527, issued May 26, 1992 to Coates et al., and U.K. Patent Application No. 9111025.4, by Graham et al. and published Dec. 4, 1991.

SUMMARY OF THE INVENTION

Accordingly, it is an object of this invention to provide mesogenic compounds and mixtures of mesogenic compounds that exhibit the smectic C* phase.

It is a further object of this invention to provide mesogenic compounds and mixtures of mesogenic compounds that exhibit the smectic A* phase.

It is a further object of this invention to provide mesogenic compounds having large spontaneous polarization, large tilt angles over a wide temperature range around ambient, improved mechanical stability, large electroclinic coefficients, tilt angles and switching times that are largely independent of temperature, and field independent switching times in the microsecond regime.

These and additional objects of the invention are accomplished by the structures and processes hereinafter described.

The present invention is a mesogenic compound having the formula:

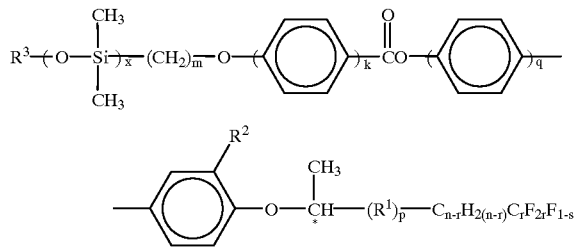

wherein $R^1$ is an ester (—COO—) group; $R^2$ is H, $NO_2$, CN, F, or Cl; $R^3$ is H, $CH_2$=CH, or $(CH_3)_3Si$; k is 1 or 2; q is 0 or 1; m is from 2 to 16; n is from 2 to 12; r is from 0 to n−1 (but not greater than 3 or 4); s=1 when r=0, s=0 when r≠0; x is from 0 to 4; and* denotes the position of a chiral carbon.

Another aspect of the present invention is a mixture comprising one of these mesogenic compounds, or two or more of these mesogenic compounds.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements, wherein.

DETAILED DESCRIPTION OF THE PREFERRED EMBODIMENTS

As is seen from the Summary of the Invention, the linear carbon chain near the chiral end of a molecule according to the invention may be partially fluorinated. However, it is generally preferred for this chain to be a minimally fluorinated chain (e.g., r=1), and more preferred for this chain to be an unfluorinated chain (i.e., r=0). Fluoride groups on this chain will generally elevate the melting point of compounds according to the invention, decreasing the operating range of such compounds.

Of the non-hydrogen $R^2$ groups, $NO_2$ is generally the most preferred, due to its ability to lower the melting point of compounds according to the invention.

For the preferred embodiments of the invention discussed below, phase transition data is given in tabular form showing where the phase transitions occur for that embodiment. For instance, the entry K −13.8 Sm C* 20.5 Sm A* 76.6 I from Table I below, indicates that this compound changes from the crystalline phase to the smectic C* phase at −13° C., from the smectic C* phase to the smectic A* phase at 20.5° C., and from the smectic A* phase to the isotropic (liquid) phase at 76.6° C.

The mPPBNn Series

One particularly useful subgroup (referred to herein as the mPPBNn series) of the mesogenic compounds of the present invention has the general formula:

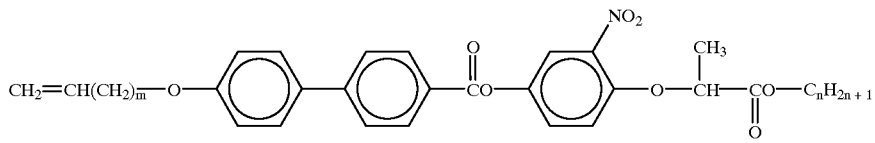

where m varies from 6 to 14 and n varies from 2 to 12. More typically, m will be from 6 to 12 and n will be from 2 to 8. As n goes above 8, different properties may be observed. Both polarization and response time vary with the values of m and n: a shorter m chain or n chain will result in a higher polarization and a slower response time.

The phase transitions of representative compounds in the mPPBNn series were measured by differential scanning calorimetry (D.S.C.), and are shown in Table I:

TABLE I

Phase Transitions of mPPBNn Compounds

| m | n | Compound | Phase Transition Temperatures (° C.) | | | | | |
|---|---|---|---|---|---|---|---|---|
| 8 | 8 | 8PPBN8 | K | −13.8 Sm C* | 20.5 | Sm A* | 76.6 | I |
| 8 | 6 | 8PPBN6 | K | 27.7 Sm C* | 32.0 | Sm A* | 74.0 | I |
| 8 | 4 | 8PPBN4 | K | 47.4 Sm C* | 54.7 | Sm A* | 74.4 | I |
| 8 | 2 | 8PPBN2 | K | 65.0 Sm C* | 66.2 | Sm A* | 79.0 | I |

Legend: K = solid crystal phase; Sm C* = ferroelectric smectic C*; Sm A* = electroclinic smectic A*; I = isotropic.

Figure 1:
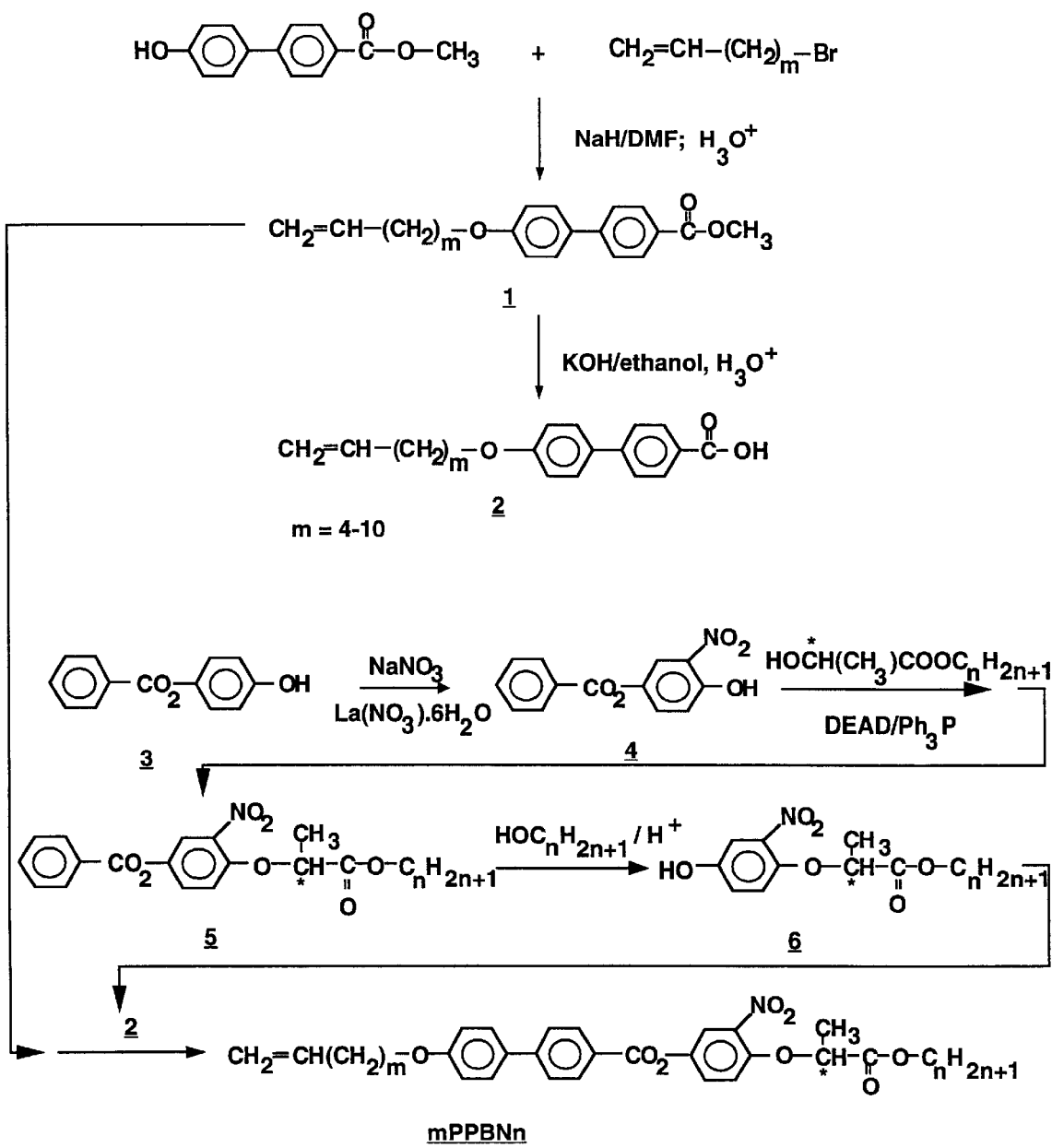
FIG. 1 shows a process for synthesizing a preferred embodiment of the invention, designated mPPBNn.

As shown in Table I, the compounds in series mPPBNn have both a smectic C* phase and a smectic A* phase. These compounds, and mixtures of these compounds, have fast switching, large polarizations, and ferroelectricity over broad temperature ranges. A synthesis scheme for the compounds in series mPPBNn is shown in FIG. 1.

The KNmn Series

Another particularly useful subgroup (referred to herein as the KNmn series) of the mesogenic compounds of the present invention has the general formula:

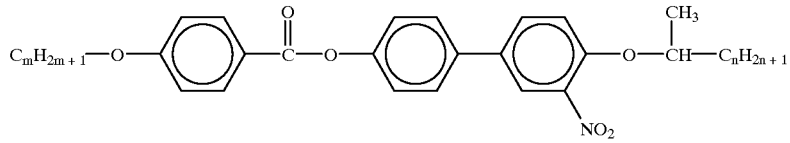

where m varies from 2 to 14 and n varies from 2 to 6. More typically, m will be from 2 to 12 and n will be from 3 to 5.

The compounds in the KNmn series do not have a stable smectic C* FLC phase: their only stable liquid crystal phase is the smectic A* phase. See Table II, below. This is a desirable feature for electroclinic materials, because the absence of a lower temperature phase enables us to supercool the smectic A* phase to ambient temperatures. The most spectacular result is that KN123(R) exhibits melting point of−5° C. and a smectic A* range of over 90° C. This is the best operating temperature range electroclinic compound known to date, and should extend the operating range of the device.

All of the compounds in the KNmn series that have been tested show fast response times ranging from 40 to 70 μs at ambient temperature. These response times would be faster at higher temperatures, where the viscosity of the liquid crystal would be lower. At least as significantly as their response times, compounds in this series have tilt angles for applied voltages of that are among the highest reported to date for any electroclinic liquid crystal. These compounds, and mixtures of these compounds, thus will be an excellent choice when fast switching and large tilt angles are desired.

The phase transitions of representative compounds in the KNmn series are shown in Table II:

TABLE II

Phase Transitions of KNmn Compounds

| m | n | Compound | Phase Transition Temperatures (° C.) | | | |
|---|---|---|---|---|---|---|
| 8 | 6 | KN86 (S) | K | 58.9 | Sm A* | 68.7 | I |
| 10 | 6 | KN106 (S) | K | 39.0 | Sm A* | 74.0 | I |
| 10 | 6 | KN106 (R) | K | 38.0 | Sm A* | 72.4 | I |
| 12 | 6 | KN126 (R) | K | 45.0 | Sm A* | 74.9 | I |
| 10 | 5 | KN105 (S) | K | 45.0 | Sm A* | 76.4 | I |
| 12 | 5 | KN125 (S) | K | 29.8 | Sm A* | 80.0 | I |
| 12 | 3 | KN123 (R) | K | −5.0 | Sm A* | 81.4 | I |
| 10 | 4 | KN104 (S) | K | 42.0 | Sm A* | 77.8 | I |
| 12 | 4 | KN124 (S) | K | 15.0 | Sm A* | 78.0 | I |

Legend: (R) = rectus enantiomer; (S) = sinister enantiomer; K = solid crystal phase; Sm A* = smectic A*; I = isotropic.

A synthesis scheme for the compounds in series KNmn is shown in FIG. 2.

The x-SiKNmn Series

Another particularly useful subgroup (referred to herein as the x-SiKNmn series) of the mesogenic compounds of the present invention has the general formula:

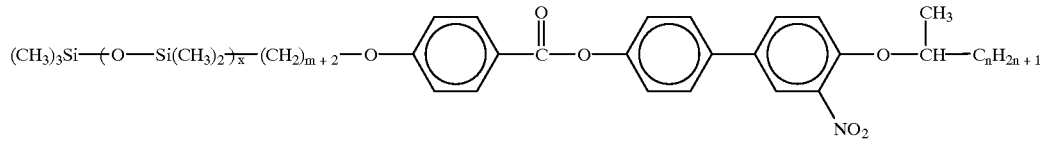

where x varies from 0 to 3 or 4, m varies from 4 to 16 and n varies from 2 to 6. More typically, x will be from 0 to 2, m will be from 4 to 10 and n will be from 2 to 5. The compounds in the x-SiKNmn series are structurally similar to those in the KNmn series, but have a silane group (and optional siloxane groups) at the non-chiral end of the molecule. Compared to the compounds in the KNmn series, these compounds have lower melting points (less than 10° C.) and larger electroclinic coefficients $d\theta/dE$.

Figure 3:
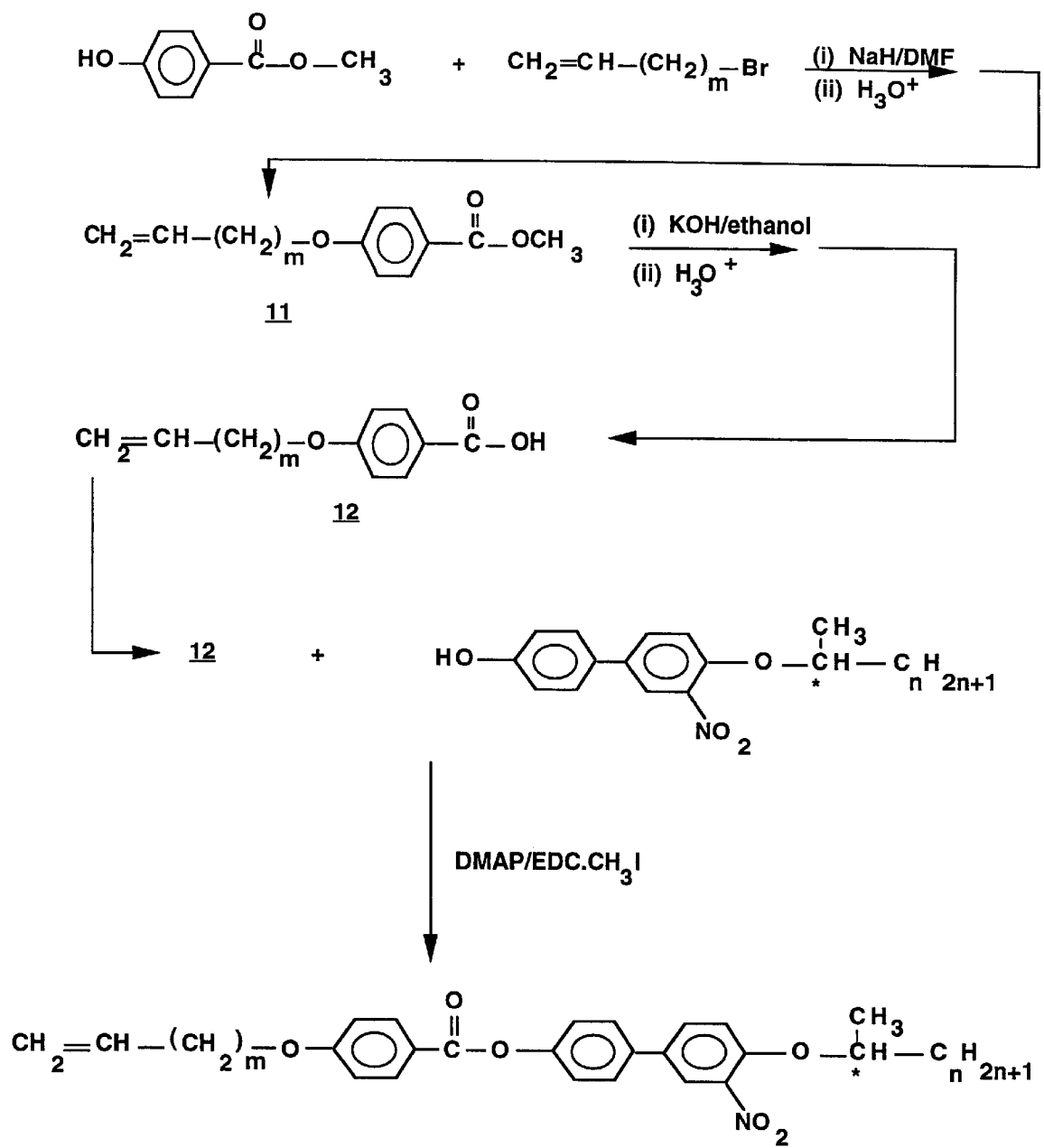
FIG. 3 shows a process for synthesizing another preferred embodiment of the invention, designated 2 KNmn.

The phase transitions of representative compounds in the x-SiKNmn series are shown in Table III:

As shown in Table III, these compounds have both a ferroelectric smectic C* phase and an electroclinic smectic A* phase. All of the materials in this series listed above have melting points less than room temperature, exhibit a stable ferroelectric phase at temperatures well below ambient temperatures and exhibit polarizations in the range of 180–300 nC/cm$^2$ at 25° C. These materials also exhibit very large tilt angle (up to 33°) in the smectic C* phase. Thus, compounds in the x-SiKNmn series are very attractive materials for ferroelectric display devices. A synthesis scheme for the compounds in series x-SiKNmn is shown in FIG. 3.

The 2KNmn Series

Another particularly useful subgroup (referred to herein as the 2KNmn series) of the mesogenic compounds of the present invention has the general formula:

TABLE III

Phase Transitions of x-SiKNmn Compounds

| x | m | n | Compound | Phase Transition Temperatures (° C.)[1] | | | | | |
|---|---|---|---|---|---|---|---|---|---|
| 0 | 6 | 5 | SiKN65 (S) | K | sub 10 | Sm C* | 48.2 | Sm A* | 51 | I |
| 1 | 6 | 5 | DSiKN65 (S) | K | sub 10 | Sm C* | 40.5 | Sm A* | 55 | I |
| 2 | 6 | 5 | TSiKN65 (S) | K | sub 10 | Sm C* | 23 | Sm A* | 55.5 | I |
| 2 | 8 | 5 | TSiKN85 (S) | K | sub 10 | Sm C* | 27 | Sm A* | 49 | I |

Legend: Si = 1 silicon atom in the molecule (i.e., x = 0); DSi = 2 silicon atoms; TSi = 3 silicon atoms; (R) = rectus enantiomer; (S) = sinister enantiomer; K = solid crystal phase; Sm C* = smectic C*; Sm A* = smectic A*; I = isotropic.
[1]Melting points have been determined to be below 10° C., but precise measurements have not been made as of the date of this writing.

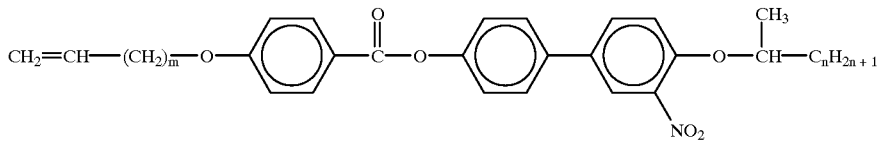

where m varies from 2 to 14 (but not 2 or 4 when n=5) and n varies from 2 to 6. More typically, m will be from 4 to 10 (but not 4 when n=5) and n will be from 2 to 5.

The compounds in the 2KNmn series are structurally similar to those in the KNmn series, but have an alkenyl group at the non-chiral end of the molecule. Compared to the compounds in the KNmn series, these compounds have lower melting points. Compare the melting point of 2KN86 (26.5° C.) with the melting point of KN106 (38° C.). Although these two compounds have the same number of carbons, their melting points differ by over 10° C.

The phase transitions of representative compounds in the 2 KNmn series are shown in Table IV:

TABLE IV

Phase Transitions of 2KNmn Compounds

| m | n | Compound | Phase Transition Temperatures (° C.) | | | | |
|---|---|----------|---|---|---|---|---|
| 6 | 5 | 2KN65 (S) | K | 27.5 | Sm A* | 61.5 | I |
| 8 | 6 | 2KN86 (R) | K | 26.5 | Sm A* | 58.8 | I |

Figure 4:
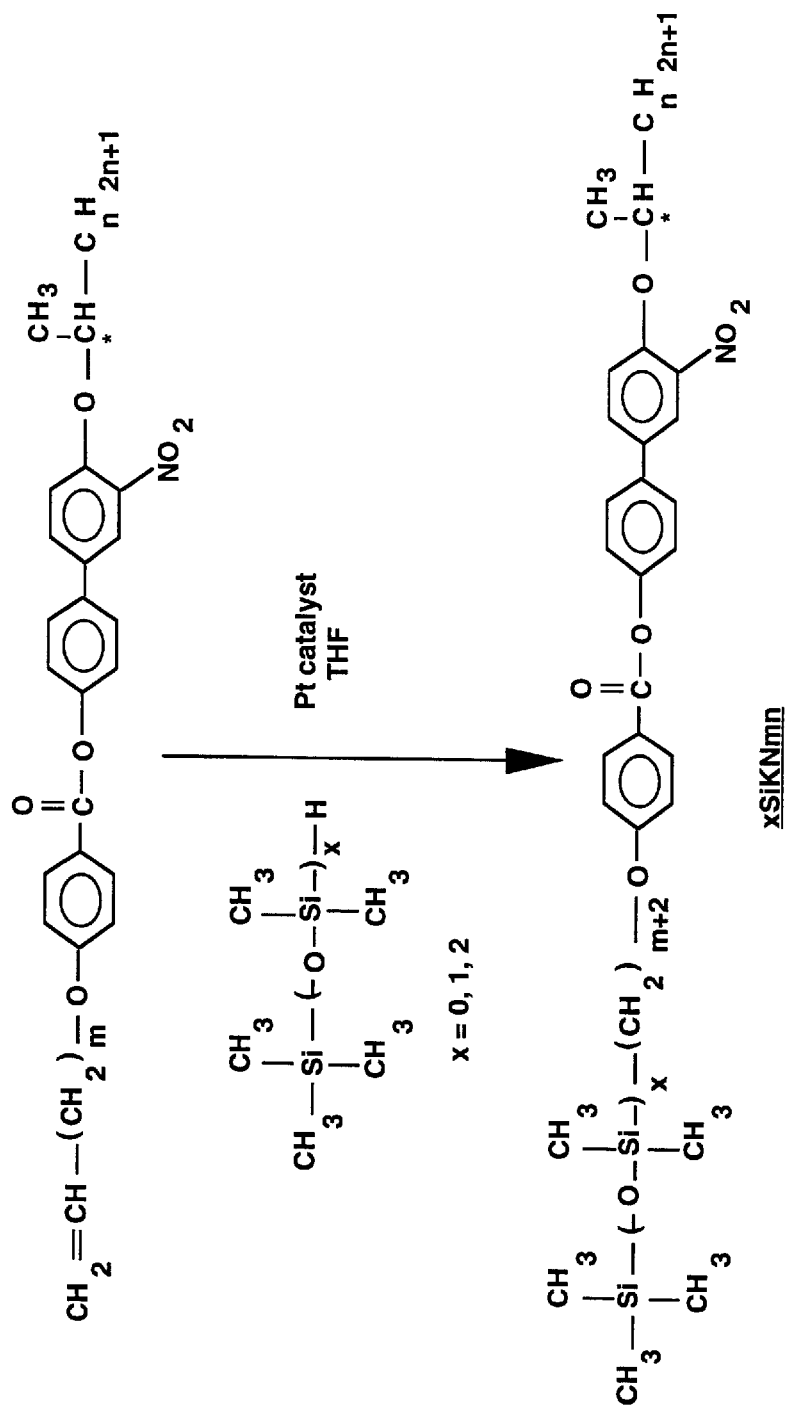
FIG. 4 shows a process for synthesizing another preferred embodiment of the invention, designated x-SiKNmn.

A feature of these materials is that, like compounds in the KNmn series, they also exhibit only the electroclinic smectic A* phase: the ferroelectric smectic C* is absent. The melting points of these compounds are quite low, making them useful for gray scale applications. A synthesis scheme for the compounds in series 2KNmn is shown in FIG. 4.

The x-SimPPBNn Series

Another particularly useful subgroup (referred to herein as the x-SimPPBNn series) of the mesogenic compounds of the present invention has the general formula:

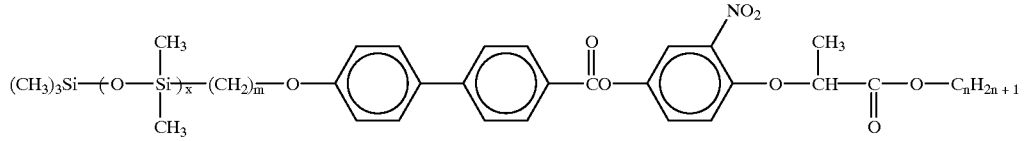

where x varies from 0 to 3, m varies from 4 to 16 and n varies from 2 to 8. AMore typically, x will be from 0 to 2, and m will be from 4 to 10. The compounds in the x-SimPPBNn series are structurally similar to those in the mPPBNn series, but have a silane group (and optional siloxane groups) at the non-chiral end of the molecule. These compounds also exhibit both smectic C* and smectic A* phases. The phase transitions of a representative compound in this series (TSi10PPBN2) are as follows:

K sub 10° C. Sm C* 34° C. Sm A* 100° C. I.

Figure 5:
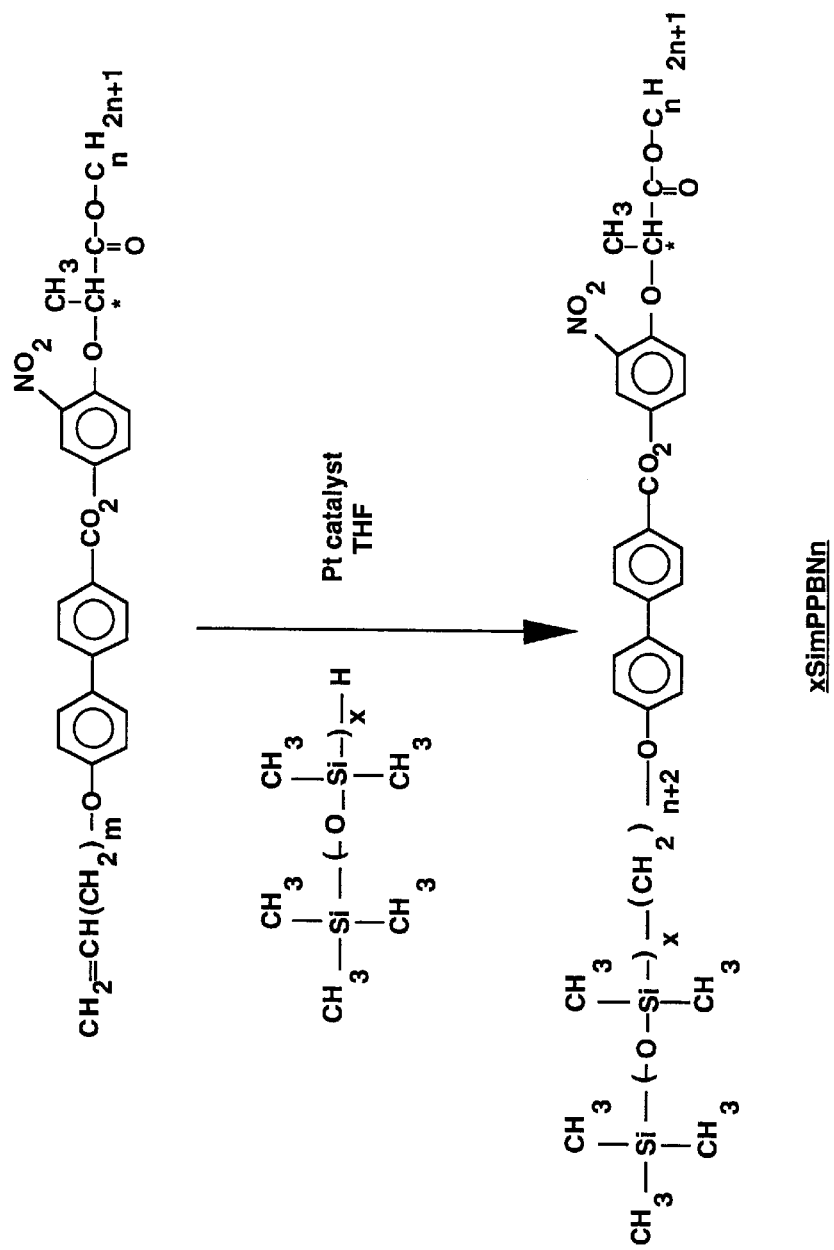
FIG. 5 shows a process for synthesizing another preferred embodiment of the invention, designated x-SimPPBNn.

A synthesis scheme for the compounds in series x-SimPPBNn is shown in FIG. 5.

Mixtures of Liquid Crystal Compounds

Skilled practitioners recognize that it is rare for a single mesogenic compound to possess optimal properties for a particular application. Skilled practitioners also recognize that once the properties of two mesogenic compounds are known, the properties of binary mixtures of these compounds may be predicted with a good deal of certainty. Likewise, the properties of more complex mixtures (e.g., ternary mixtures) of mesogenic compounds may be predicted from the properties of the components of these mixtures. Mixtures of mesogenic compounds may be selected to have desirable properties that no known single mesogenic compound can provide. Consequently, mixtures of mesogenic compounds typically are used in applications.

To secure the benefits of the present invention, it is preferred to mix a mesogenic compound according to the invention with another mesogenic compound, to form a mixture of mesogemc compounds, using the knowledge of a person of ordinary skill in the art. This other mesogenic compound may also be a mesogenic compound according to the invention, or it may be a known mesogenic compound. Also, it is preferred to mix a mesogenic compound according to the invention with at least two other mesogenic compounds, to form a complex mixture of mesogenic compounds, using the knowledge of a person of ordinary skill in the art, Those other mesogenic compounds may be independently selected from the mesogenic compounds according to the invention and the known mesogenic compounds. For instance, a skilled practitioner would recognize that by mixing a first electroclinic liquid crystal having a low melting point and a low transition temperature to the isotropic state with a second electroclinic liquid crystal having a high melting point and a high transition temperature to the isotropic state, a mixture can be obtained that will have a broader operability range than either the first electroclinic liquid crystal or the second electroclinic liquid crystal alone. These mixtures may further include one or more known additives to mixtures of mesogenic compounds. For example, viscosity-reducing agents are frequently included in mixtures of mesogenic compounds. See, e.g., U.S. Pat. No. 4,118,335.

Having described the invention, the following examples are given to illustrate specific applications of the invention, including the best mode now known to perform the invention. These specific examples are not intended to limit the scope of the invention described in this application.

EXAMPLES

Sample mixtures were produced by weighing out appropriate masses of the components into microcentrifuge tubes and then heated to a temperature above the clearing temperature and mixed thoroughly to ensure complete mixing. The samples were then cooled and stored under dry argon.

Electro-optic measurements were preformed with used commercially prepared sample cells from E.H.C. Company, Ltd., Japan. They were 10 μm thick, with ITO electrodes forming a 4 mm×4 mm square active area, and their polymer coated surfaces were rubbed to obtain planar alignment of the FLC materials. The cells were filled in vacuo at a temperature close to the isotropic-smectic A* (I-Sm A*) transition. By heating the sample just enough to permit capillary action to fill the cell, it's viscosity remained high enough that filling proceeded slowly and could be stopped when the electrodes were covered. This technique helped prevent thermal degradation and conserved the locally synthesized FLC materials.

The rubbed polymer coatings and the application of a square-wave electric field (E,) as the sample was cooled from the Sm A* to the Sm C* phase combined to produce well aligned samples which displayed nearly uniform planar textures. Although the 10 $\mu$m samples were too thick to permit suppression of the samples' helices by surface interactions alone, it was possible to unwind the helices completely by applying a sufficiently large electric field (typically E>3 Volts/$\mu$m). All measurements used an applied field greater than this "threshold" value.

The cell's temperature was controlled to ±0.05° C. in a microscope hot stage (Mettler FP80 HT). The spontaneous polarization (P) measurements were made using the triangular wave technique. The output of a function generator (Wavetek 271) was fed to a high-output amplifier (Trek 601B-2) which excited an RC circuit consisting of the liquid crystal cell and a high precision series load resistance. The voltage drop across this resistance was recorded on a digital storage scope (Hitachi VC-6165), and the waveforms were retrieved, stored, and analyzed on a 386-based computer. The frequencies of the applied triangular wave, with an amplitude of 10 V, varied from 500 Hz to 0.5 Hz: the samples became more viscous at lower temperatures and the frequency had to be decreased to allow the samples to switch completely before the applied field reversed.

All measurements were made as the samples were cooled. Ps was measured first, then the sample was reheated and the optical tilt angle ($\theta$) determinations were made. Optical response time measurements $\tau$ then followed.

The optical tilt angle determinations were performed on a polarizing light microscope (Nikon Optiphot) with a standard halogen lamp light source. Inclusion of a GG-400 edge filter in the microscope's illumination path blocked UV light and eliminated the sample degradation. A low frequency (0.1 Hz) square wave voltage was applied to the cell. The intensity of the transmitted light was measured with a photodiode coupled to an amplifier (UMT 101C) and the output was read on a digital multimeter (Keithley 197). The angle of rotation of the microscope stage from extinction in one switched state (E in one direction) to extinction in the other switched state (E in the opposite direction) was determined. This angle is equal to the cone angle of the director and one half its value gives the optical tilt angle $\theta$.

Optical response time measurements (switching times) were determined by connecting the photodiode amplifier to the oscilloscope and recording the transmitted intensity as a square wave electric field was applied to a sample.

Example 1

Synthesis and Properties of Compounds in the mPPBNn Series

The compounds listed in Table I were synthesized as outlined in FIG. 1. The synthesis of (R)-4'-(1-carbobutoxy-ethyloxy)-3-nitrophenyl-4-[4-(9-decenyloxy)phenyl] benzoate (8PPBN4, m=8, n=4) typifies the synthesis of the compounds listed in Table I. All other materials from the series were made following the same procedure.

To a mixture of the phenol derivative 6 3.65 g (5.93 mmol), 2 2.09 g (5.93 mmol), and DMAP 61 mg (0.49 mmol) in 100 mL of dichloromethane was added 1-(3-dimethylaminopropyl)-3-ethyl-carbodiimide-methiodide (EDC.CH$_3$I), 2.43 g (8.2 mmol). The mixture was stirred for 24 hours at room temperature. After dilution with dichloromethane, the organic phase was washed with water, a saturated solution of sodium bicarbonate, brine and finally dried over sodium sulfate. The solvent was evaporated and the residue was purified by column chromatography on silica gel (¼ ethyl acetate/hexane) followed by a recrystallization from ethanol to yield 2.44 g (61%). The structure was checked by $^1$H NMR and elementary analysis.

The materials exhibit polarization values exceeding 300 nC/cm$^2$ and response times in the range from 100 to 200 microseconds at ambient temperatures. Thus the mPPBNn compounds, and in particular the 10PPBNn compounds show properties which are attractive from the point of view of ferroelectric display device applications.

Figure 6:
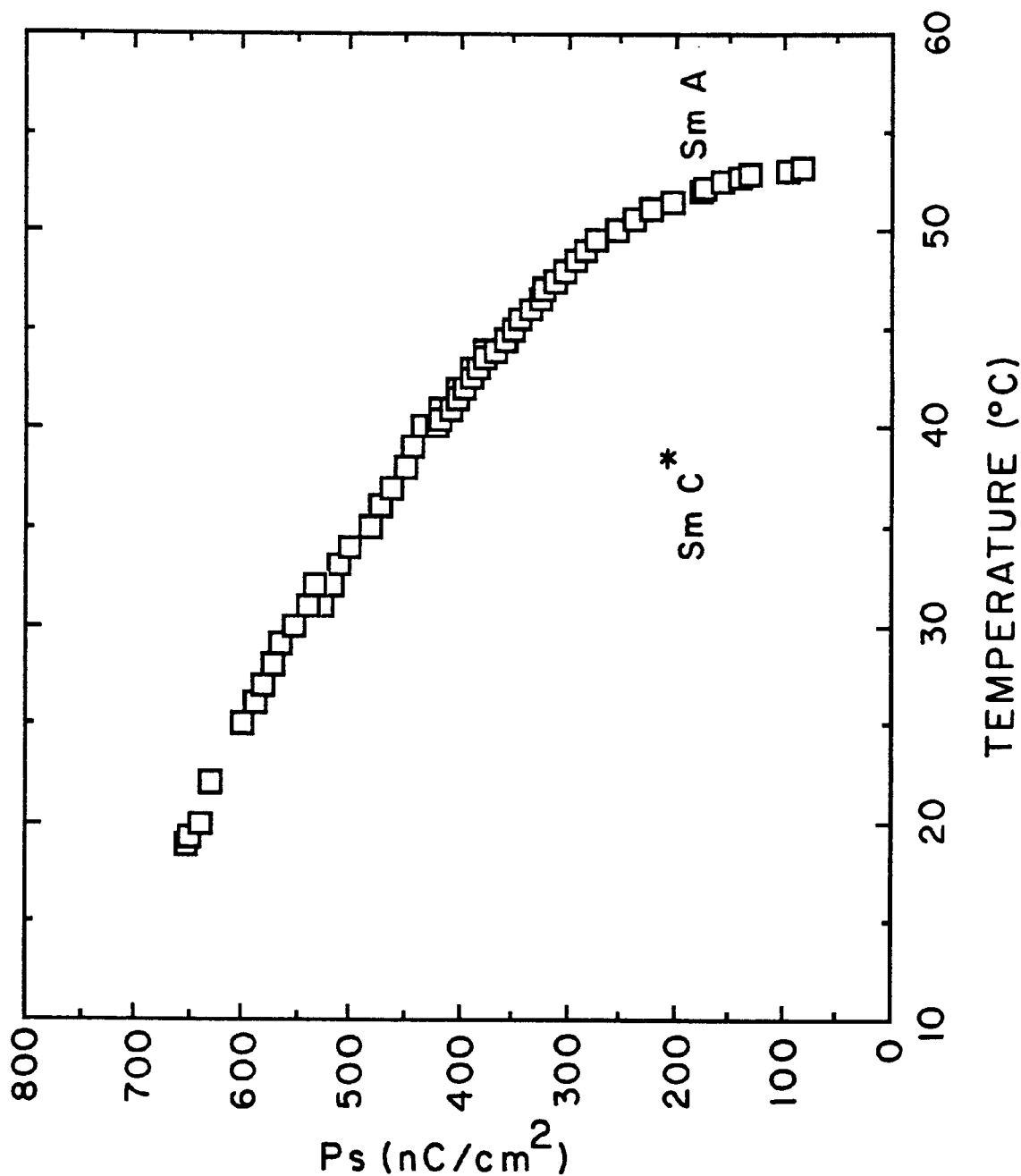
FIG. 6 shows the temperature dependence of polarization in the ferroelectric smectic C* phase for a preferred embodiment of the invention, designated 8PPBN4.

All the materials exhibited large polarization values and fast response times. The temperature dependence of polarization in the ferroelectric smectic C* phase for a representative compound is given in FIG. 6. In addition to being useful in themselves, the compounds in this series are also useful as precursors for compounds in the x-SimPPBNn series. See Example 5 below.

Example 2

Synthesis and Properties of Compounds in the KNmn Series

Figure 2A:
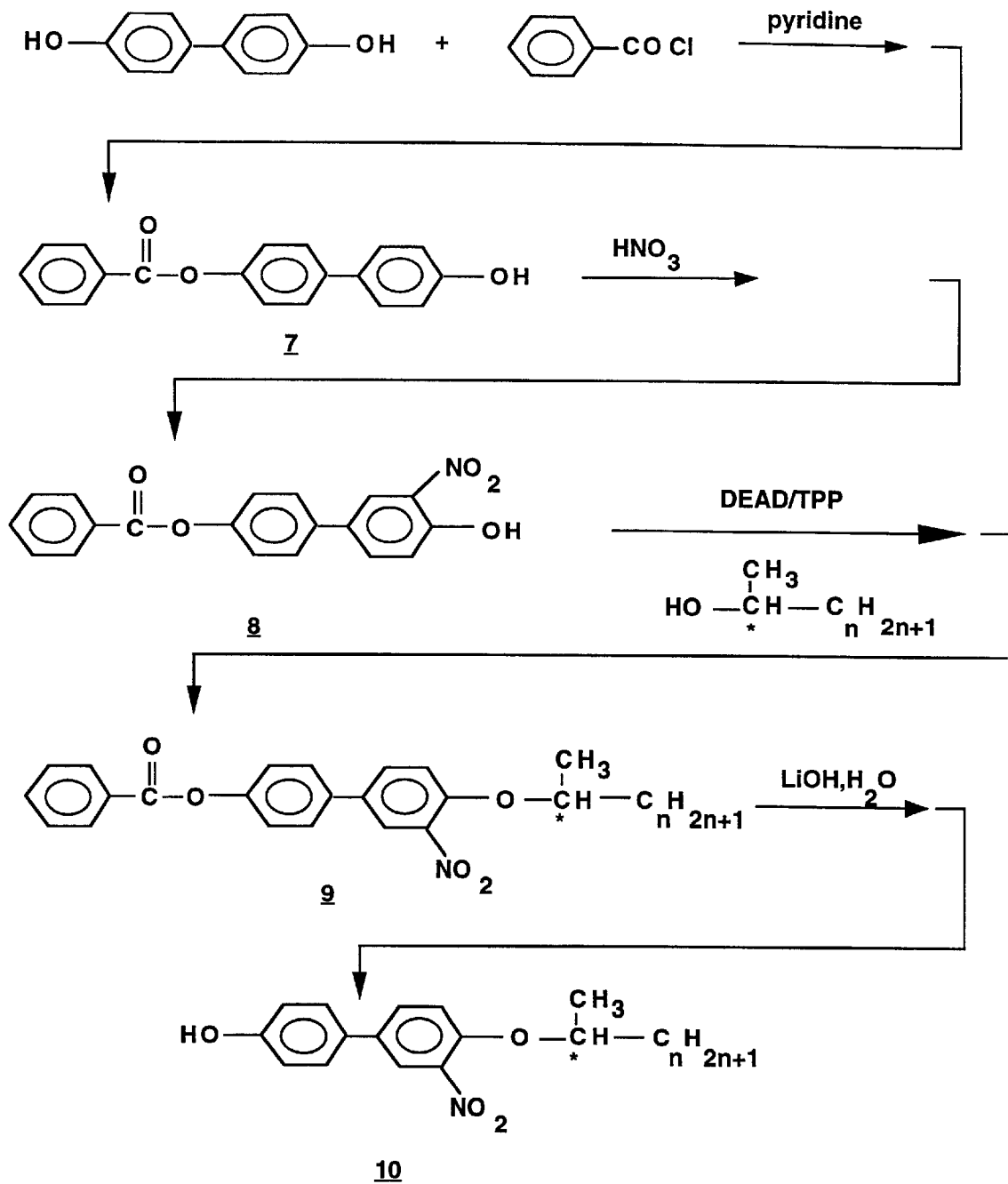
FIG. 2A shows a process for synthesizing a precursor for several preferred embodiments of the invention.
Figure 2B:
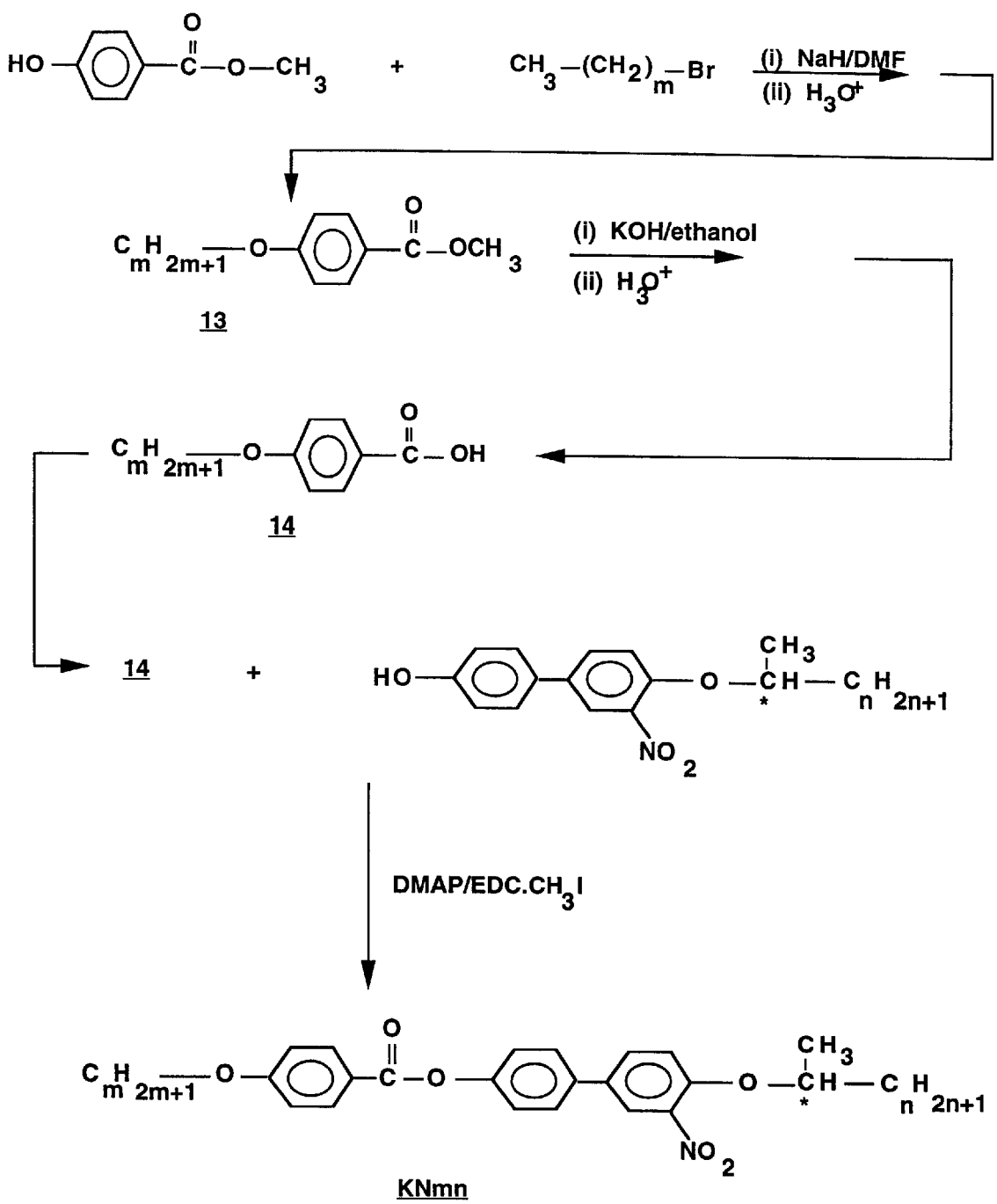
FIG. 2B shows a process for synthesizing another preferred embodiment of the invention, designated KNmn.

The compounds listed in Table II were synthesized as outlined in FIGS. 2A and 2B: FIG. 2A outlines the synthesis of the chiral phenol precursors, and FIG. 2B outlines the synthesis of the nonchiral acid precursors, and the condensation of the acids and the phenols. The final condensation and purification steps leading to the compounds listed in Table II were performed following the same procedure described in Example 1.

As noted above, all these materials exhibit only the electroclinic smectic A* phase. The electroclinic response times and tilt angles of these compounds are given in Table V.

TABLE V

Electroclinic response time and induced tilt angle at 25° C. for the KNmn compounds

| m | n | Compound | Response time ($\mu$s) | Tilt angle (°) |
|---|---|---|---|---|
| 8 | 6 | KN 86 (S) | 58 | 6.5 |
| 10 | 6 | KN106 (S) | 70 | 12.5 |
| 10 | 6 | KN106 (R) | 51 | 15 |
| 12 | 6 | KN126 (R) | — | 10 |
| 10 | 5 | KN105 (S) | 48 | 7.1 |
| 12 | 5 | KN125 (S) | 40 | 11 |
| 12 | 3 | KN123 (R) | 50 | 2.5 |
| 10 | 4 | KN104 (R) | 71 | 11 |
| 12 | 4 | KN124 (S) | 70 | 10 |

Figure 7:
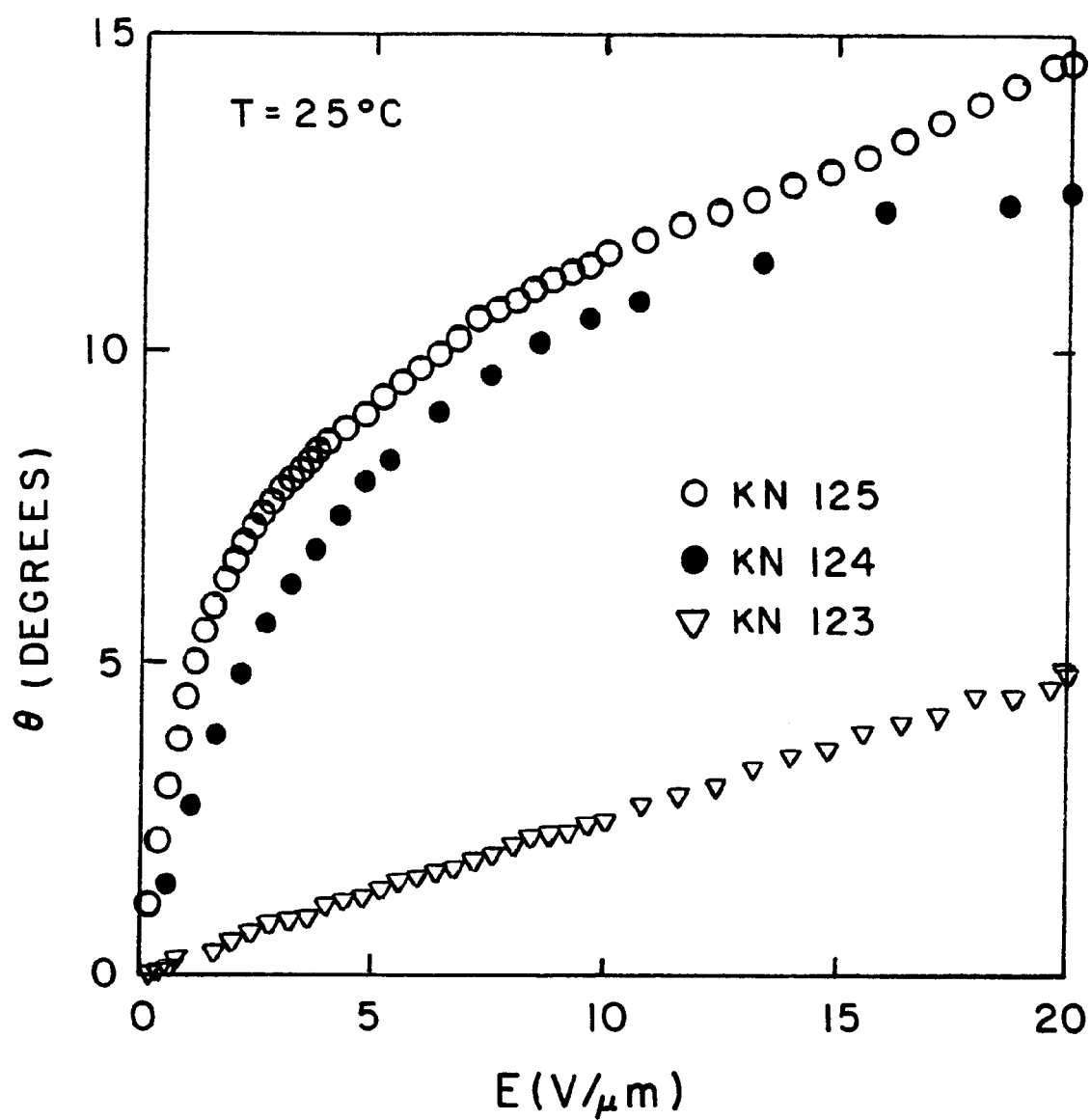
FIG. 7 shows the tilt angle as a function of applied field for three compounds in a preferred embodiment of the invention, designated KNmn.

The tilt angle at 25° C. as a function of applied field is shown in FIG. 7 for KN123, KN124, and KN125.

Example 3:

Synthesis and Properties of Compounds in the 2KNmn Series

The compounds listed in Table IV were synthesized as outlined in FIG. 3. The chiral phenol precursors were synthesized as outlined in FIG. 2A. In addition to being useful in themselves, the compounds in this series are also useful as precursors for compounds in the x-SiKNmn series. See Example 4 below.

Example 4

Synthesis and Properties of Compounds in the x-SiKNmn Series

The compounds listed in Table III were synthesized as outlined in FIG. 4. The synthesis of 4-[3'-nitro-4'-((R)-1-methylhexyloxy)phenyl]phenyl 4-(6-heptylmethyltrisiloxyhexyloxy) benzoate (TSiKN65) typifies the synthesis of the compounds listed in Table III. All other materials from the series were made following the same procedure.

To a solution of heptamethylsiloxane (0.4 g, 1.8 mmol) and 0.62 g (1.16 mmol) of 2KN65, dissolved in 30 mL of dry THF, were added 5 mg of dicyclopentadienylplatinum (II) chloride catalyst. The reaction mixture was stirred at 60° C. under nitrogen for 24 hours. The solvent was removed and the crude product was purified by column chromatography on silica gel (eluent: hexane/ethyl acetate 90/10). The product was further purified by two crystallizations in ethanol to give TSiKN65 in 70% yield.

Figure 8:
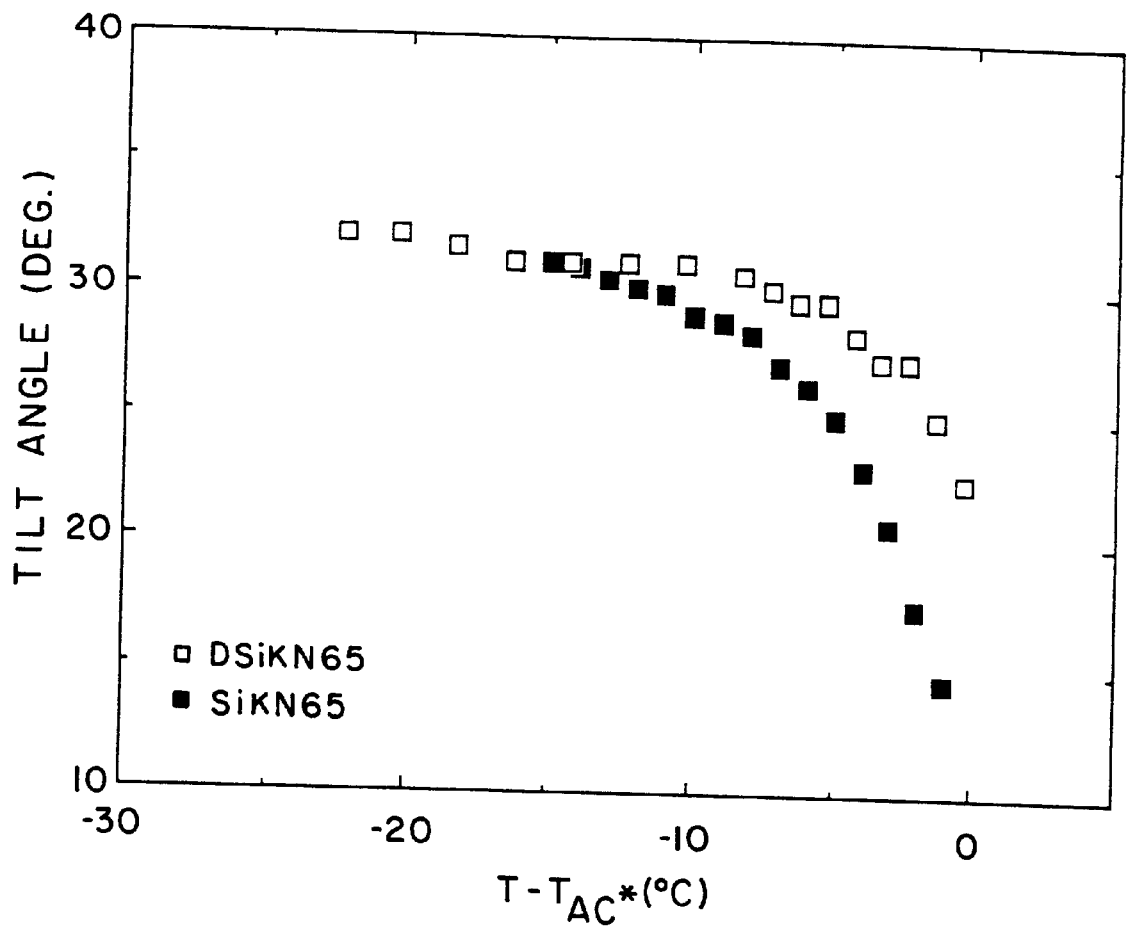
FIG. 8 shows the temperature dependence of the tilt angle for two representative compounds in a preferred embodiment of the invention, designated SiKN65 and DSiKN65.

The temperature dependence of the induced tilt angle for two representative compound in this series, SiKN65 and DSiKN65, are shown in FIG. 8. In FIG. 8, the x-axis is the relative temperature $T-T_{AC}$, where T is the sample temperature and $T_{AC}$ is the temperature of the Sm A*→Sm C* transition for the sample. This figure illustrates the large tilt angles (up to 33°) for these compounds in the smectic C* phase.

Figure 9:
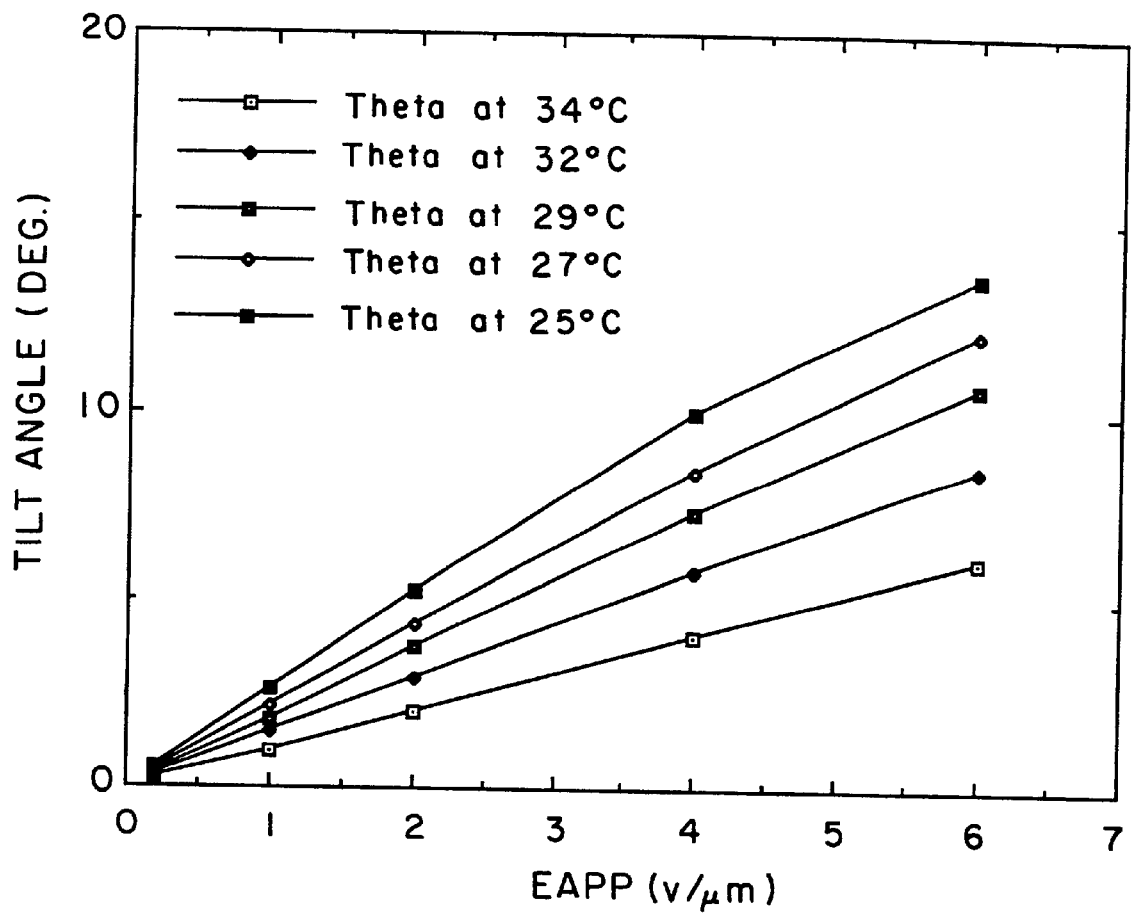
FIG. 9 shows the tilt angle as a function of applied field for a preferred embodiment of the invention, designated TSiKN65, at varying temperatures.
Figure 10:
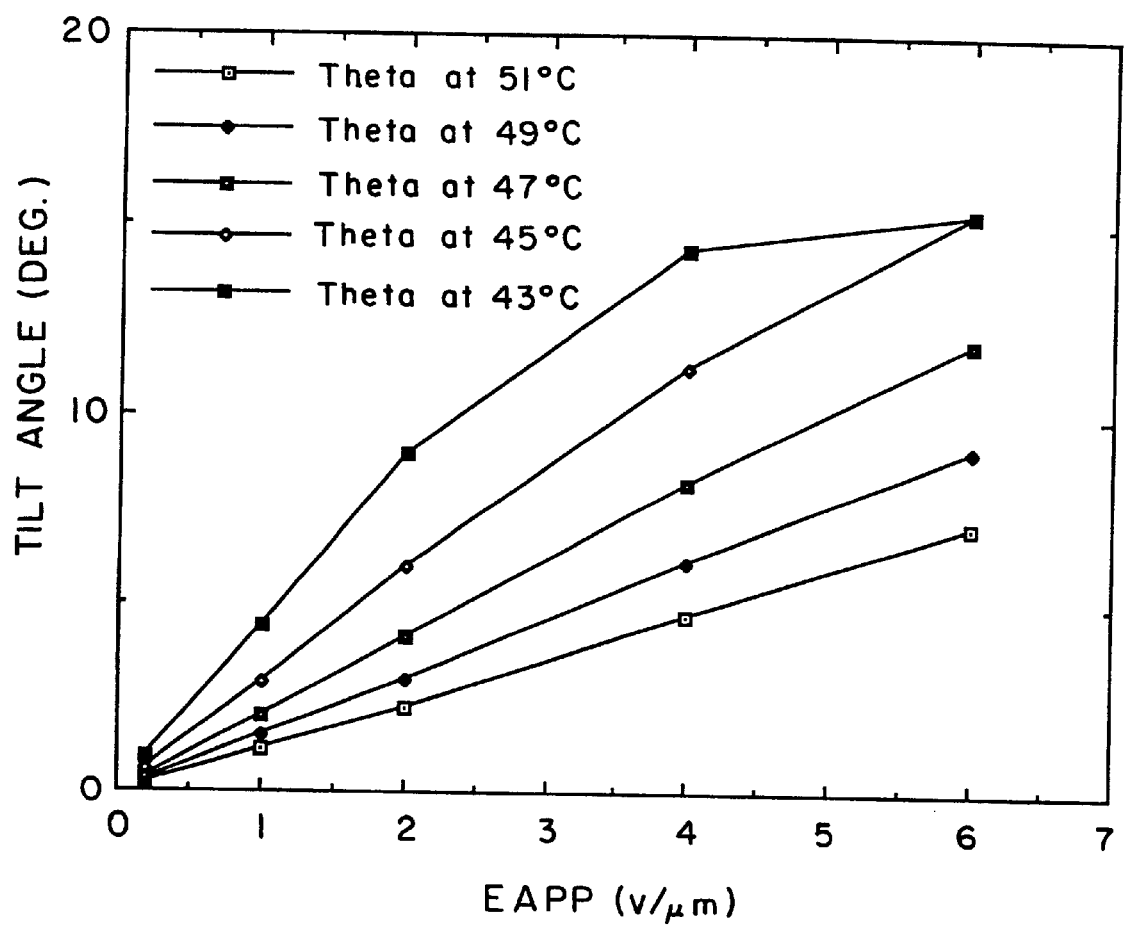
FIG. 10 shows the tilt angle as a function of applied field for a preferred embodiment of the invention, designated DSiKN65, at varying temperatures.

The induced tilt angle as a function of applied field at a variety of temperatures for a representative compound in this series, TSiKN65, is shown in FIG. 9. The induced tilt angle as a function of applied field at a variety of temperatures for another representative compound in this series, DSiKN65, is shown in FIG. 10. These two figures illustrate the exemplary electroclinic coefficients for these materials.

Example 5

Synthesis and Properties of Compounds in the x-SimPPBNn Series

The compounds listed in Table V were synthesized as outlined in FIG. 5. Condensation and purification were as described in Example 2.

Example 6

Properties of Mixtures of KN105 and KN125

A series of binary mixtures of KN105 and KN125 were prepared, with the mole fraction (χ) of KN125 in these mixtures ranging from 0.0 to 1.0.

The crystal→chiral Sm A* phase transition temperature is denoted herein as the melting temperature, $T_M$, and the chiral Sm A*→isotropic transition temperature is denoted herein as $T_I$. The latent heat, ΔH, at $T_M$ was measured to be ΔH=32 J/g for KN125 and ΔH=60 J/g for KN105. The molecular weights of the KN125 and KN105 compounds are 617 and 589, respectively. Binary mixtures were formulated by weighing the individual compounds in a vial, and subsequently heating the vial above $T_I$. The sample was then vigorously agitated in the liquid phase for 5 minutes. These materials were loaded into prefabricated 10 μm sample cells (EHC Company, Japan) without further processing. The indium tin oxide (ITO) coated glass was processed with an overlying rubbed polyimide surface to facilitate uniform homogeneous alignment. The temperature of the sample was controlled with a Mettler hot stage.

The chiral Sm A* phase in both the KN125 and KN105 compounds was found to supercool to sub-ambient temperatures for several hours (in the case of KN105) or days (in the case of KN125) before crystallization. Lowering $T_M$ below room temperature, however, is more desirable for applications, rather than relying on a supercooled phase. With this goal in mind, several binary mixtures of KN125 and KN105 were prepared, to maximize the temperature range of the chiral Sm A* phase.

Figure 11:
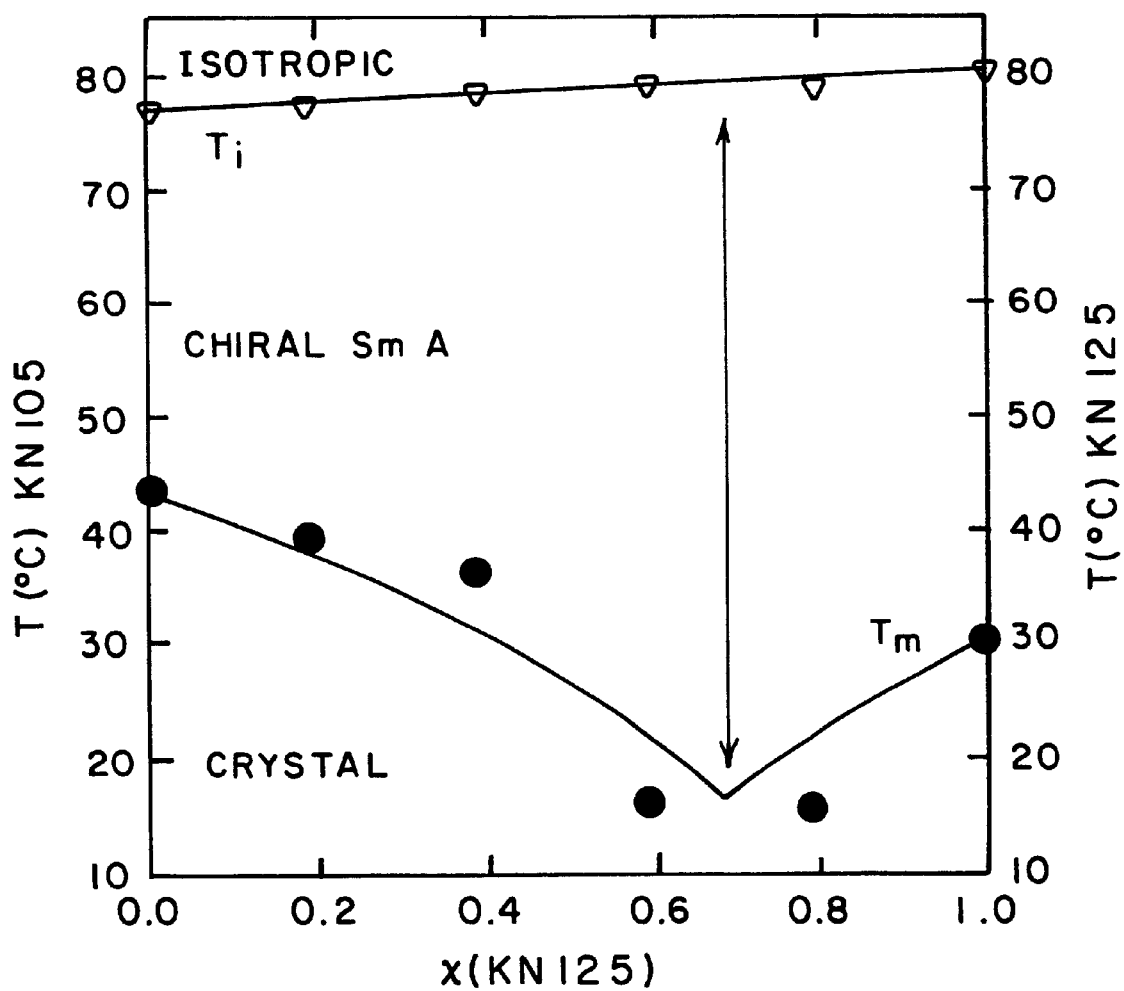
FIG. 11 shows a phase diagram for binary mixtures of two compounds according to the invention, designated KN105 and KN125.

The transition temperatures are presented in FIG. 11 for the KN125 and KNl05 compounds, and their corresponding mixtures. The solid line in FIG. 11 denotes a theoretical curve generated from the simple Schoeder-van Laar equation, $T_i = \Delta H_{fi}/[\Delta H_{fi}/T_{fi} - R\ln(\chi_i)]$, where $\Delta H_{fi}$ is the latent heat of the ith component, $T_{fi}$ is the melting temperature of the ith component, χi is the mole fraction of the ith component, and $T_i$ is the melting temperature of the mixture. This simple theory can be used to make a rough estimate of the phase behavior of the KN125/KN105 binary mixture using the relations $T_1=T_2=T_M$ (mix) and χ1+χ2=1. For the $T_1$, the solid line that fits the data is generated from the expression $T_1=\chi_i T_{Ii}$ where $T_I$ is the chiral Sm A*–isotropic transition temperature for the mixture.

Figure 12:
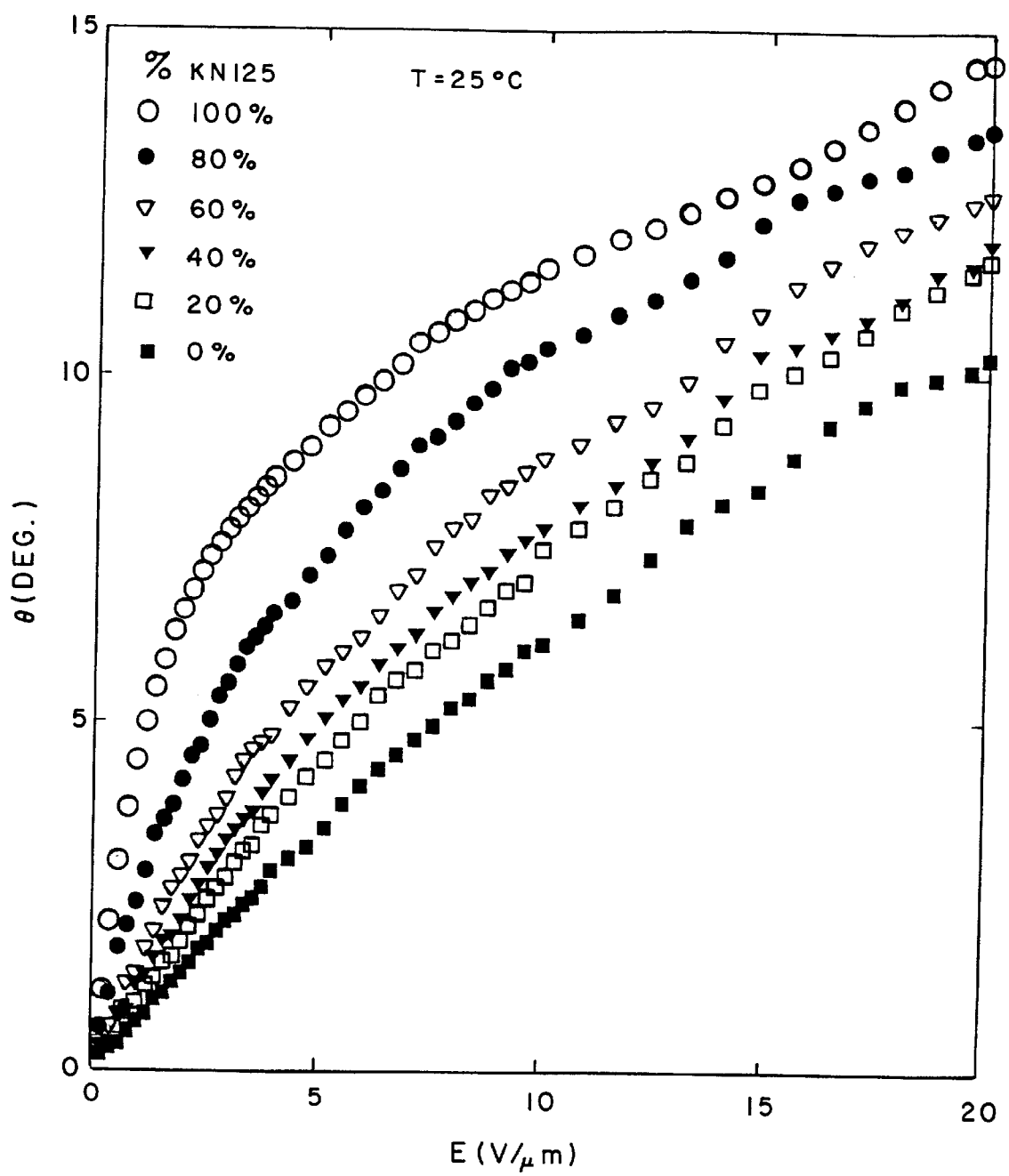
FIG. 12 shows the tilt angle as a function of electric field for a range of binary mixtures of KN105 and KN125.
Figure 13:
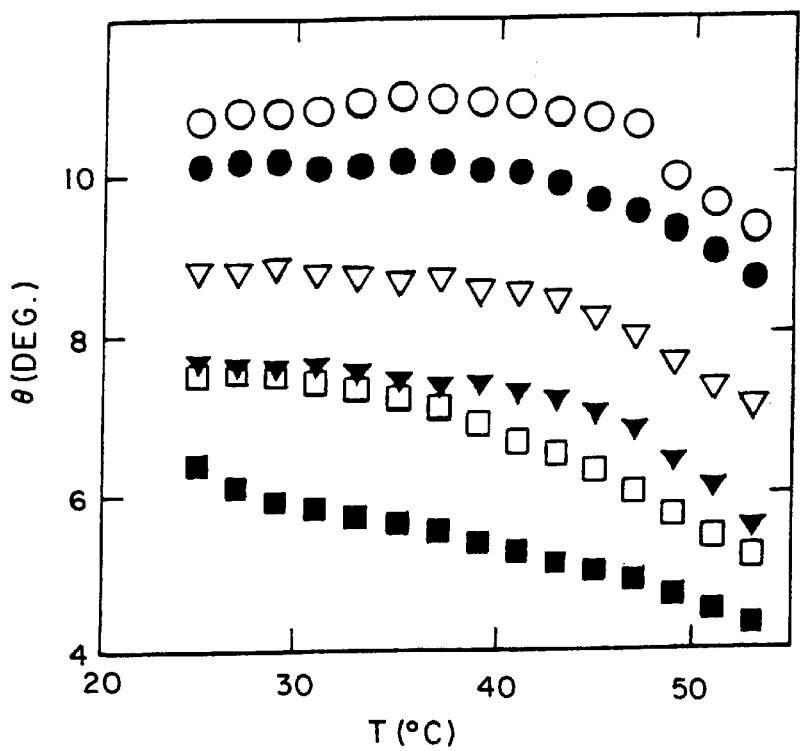
FIG. 13 shows the tilt angle as a function of temperature for a range of binary mixtures of KN105 and KN125.
Figure 14:
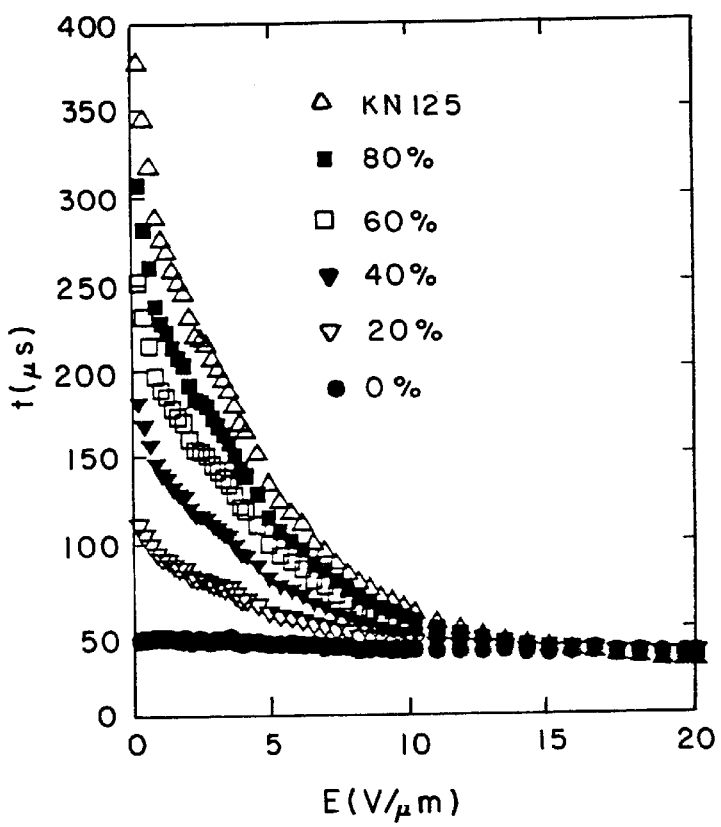
FIG. 14 shows the switching time as a function of electric field for a range of binary mixtures of KN105 and KN125.

The most impressive feature evident of FIG. 11 is the very broad chiral Sm A* phase at the eutectic point. The chiral Sm A* phase extends over a roughly 65 K temperature interval with no underlying tilted phase (Sm C* phase). The mixture with the broadest temperature range and lowest value of $T_M$ is, of course, the most desirable for applications. The tilt angle as a function of electric field is presented in FIG. 12, the tilt angle as a function of temperature is presented in FIG. 13, and the switching time as a function of electric field is presented in FIG. 14.

Example 7

Properties of Mixtures of KN124 and KN125

Figure 15:
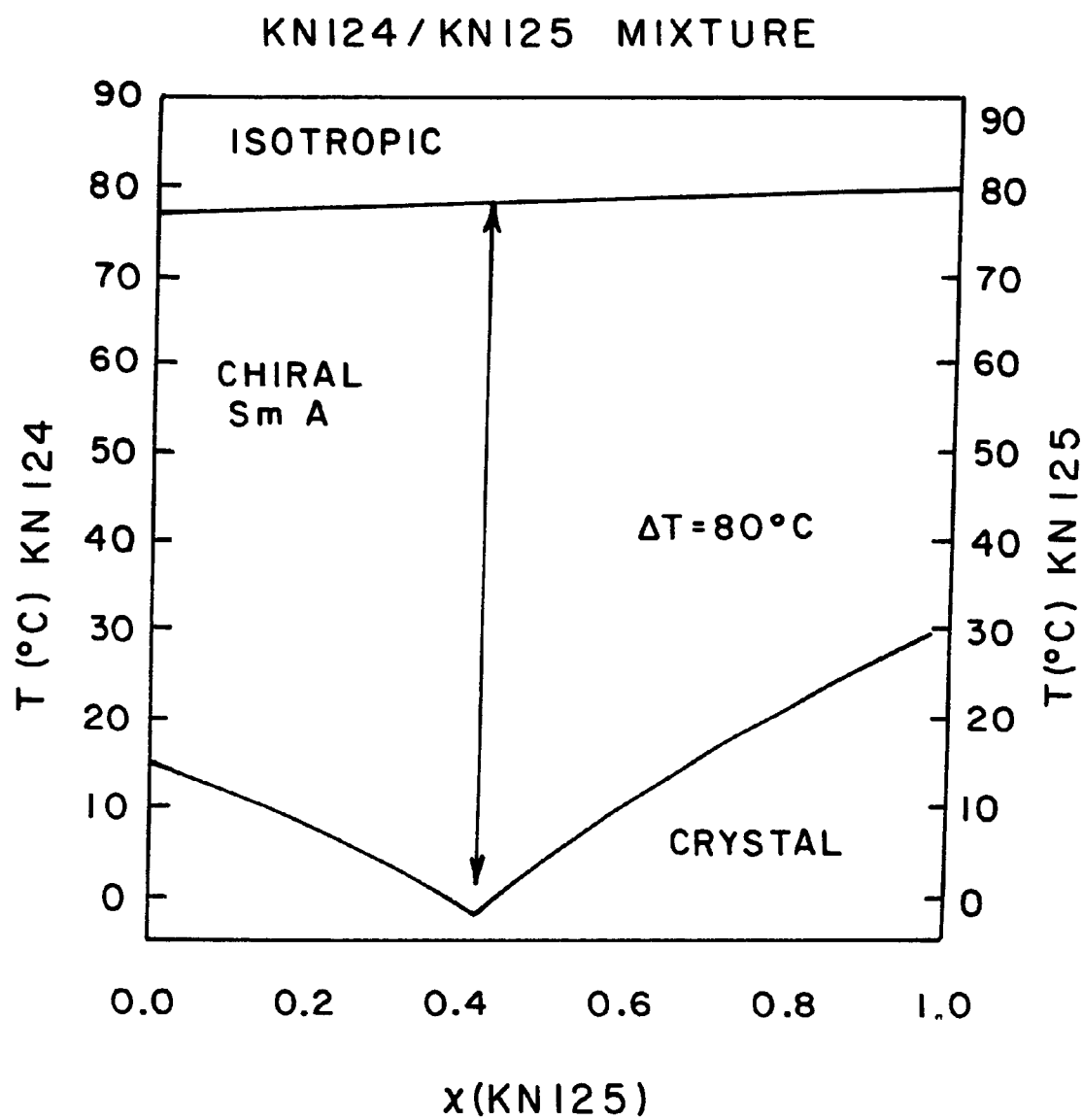
FIG. 15 shows a phase diagram for binary mixtures of two compounds according to the invention, designated KN125 and KN124.

The next example, and perhaps the most promising for large operational temperature range applications that must go to sub-zero Celsius temperatures, are the KN125/KN124 mixtures. A phase diagram based on the ΔH, molecular weight, and melting and isotropic phase transition temperatures of the pure KN125 and KN124 compounds is presented in FIG. 15. The most unique feature of the eutectic KN124/KN125 mixture is that it has a sub-zero melting point and a chiral smectic A* phase that is stable over a roughly 80° C. temperature range; this is believed to be the largest chiral smectic A* temperature range ever reported. The other unique feature of the KN124/KN125 mixtures is that the tilt angles of the two pure compounds (shown in FIG. 7) are very similar in magnitude. Therefore there is a negligible sacrifice of the tilt angle suffered when preparing mixtures of these compounds.

Obviously, many modifications and variations of the present invention are possible in light of the above teachings. It is therefore to be understood that, within the scope of the appended claims, the invention may be practiced otherwise than as specifically described.

What is claimed is:

1. A mesogenic compound having the formula:

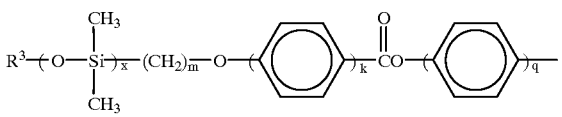

-continued

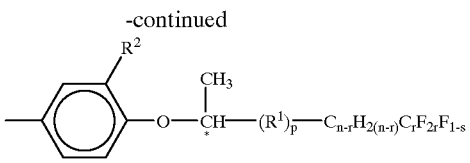

wherein R¹ is an ester group, R² is NO₂, R³ is CH₂=CH, k is 2, q is 0, m is from 6 to 14, n is from 2 to 12, p is 1, r is from 0 to 4, s=1 when r=0, s=0 when r≠0, x is 0, and * denotes the position of a chiral carbon.

2. The mesogenic compound of claim 1, wherein m is from 6 to 12, n is from 2 to 8, and r is 0.

3. A mesogenic compound having the formula:

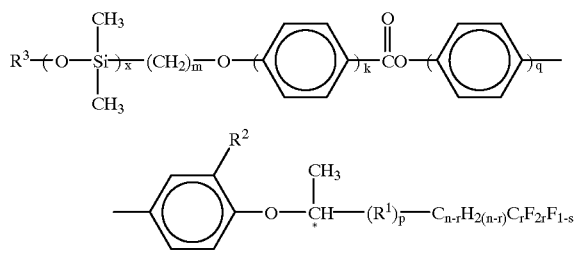

wherein R¹ is an ester group, R² is NO₂, R³ is H, k is 1 q is 1, m is from 6 to 14, n is from 2 to 12, p is 0, r is from 0 to n−1 (but not greater than 3 or −4), s=1 when r=0, s=0 when r≠0, r=0 to 4 when x=0, r=1–4 when x=0 x is 0, and * denotes the position of a chiral carbon.

4. The mesogenic compound of claim 3, wherein n is from 3 to 5 and r is 0.

5. A mesogenic compound having the formula:

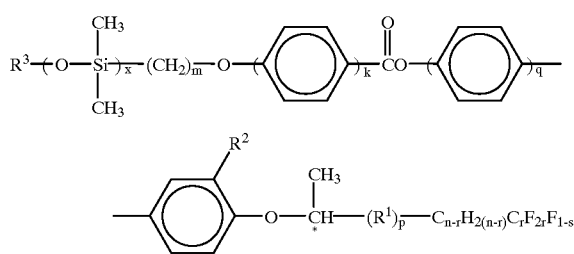

wherein R¹ is an ester group, R² is NO₂, R³ is (CH₃)₃Si, k is 1, q is 1, m is from 6 to 14, n is from 2 to 12, p is 0, r is from 0 to 4, s=1 when r=0, s=0 when r≠0, x is from 0 to 4, and * denotes the position of a chiral carbon.

6. The mesogenic compound of claim 5, wherein m is from 6 to 8, n is from 2 to 5, r is 0, and x is from 0 to 2.

7. A mesogenic compound having the formula:

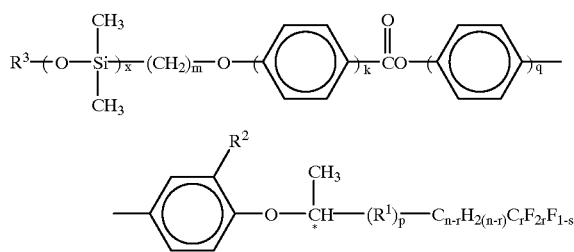

wherein R¹ is an ester group, R² is NO₂, R³ is CH₂=CH, k is 1, q is 1, m is from 6 to 14, n is from 2 to 12, p is 0, r is from 0 to 4, s=1 when r=0, s=0 when r≠0, x is from 0 to 4, and * denotes the position of a chiral carbon.

8. The mesogenic compound of claim 7, wherein m is from 6 to 10, n is from 2 to 5, and r is 0.

9. A mesogenic compound having the formula:

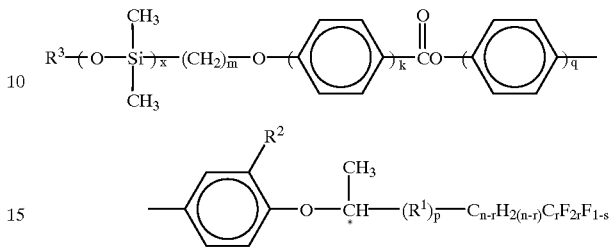

wherein R¹ is an ester group, R² is NO₂, R³ is (CH₃)₃Si, k is 0, q is 0, m is from 6 to 14, n is from 2 to 12, p is 1, r is from 0 to 4, s=1 when r=0, s=0 when r≠0, x is from 0 to 4, and * denotes the position of a chiral carbon.

10. The mesogenic compound of claim 9, wherein m is from 6 to 8, r is 0, and x is from 0 to 2.

11. A mixture comprising a first mesogenic compound having the formula:

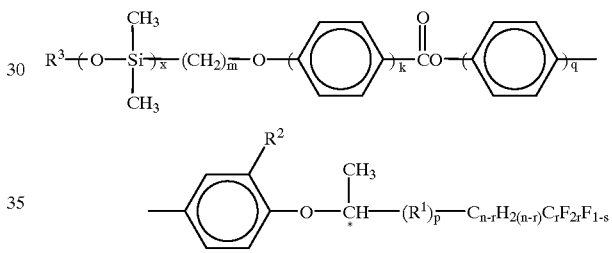

wherein R¹ is an ester group, R² is NO₂, CN, F, or Cl, R³ is H, CH₂=CH, or (CH₃)₃Si, k is 1 or 2, q is 0 or 1, m is from 2 to 16, n is from 2 to 12, p is 0 or 1, when x=0, r=0 to 4, when x=0, r=1 to 4 s=1 when r=0, s=0 when r≠0, x is from 0 to 4, and * denotes the position of a chiral carbon, and further comprising a second mesogenic compound, wherein said second mesogenic compound has the formula:

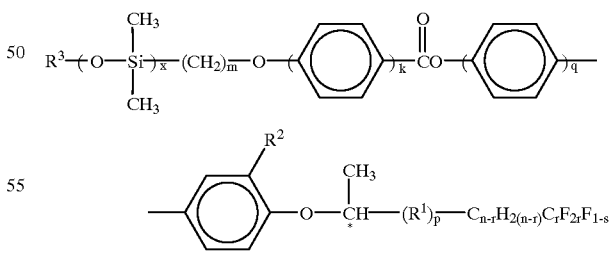

wherein R¹ is an ester group, R² is NO₂, R³ is H, CH₂=CH, or (CH₃)₃Si, k is 1 or 2, q is 0 or 1, m is from 2 to 16, n is from 2 to 12, p is 0 or 1, when x=0, r=0 to 4, when x=0, r=1 to 4 s=1 when r=0, s=0 when r≠0, x is from 0 to 4, and * denotes the position of a chiral carbon and wherein R², R³, k, q, m, n, p, and x for said second mesogenic compound are selected independently from R², R³, k, q, m, n, p, and x for said first mesogenic compound.

12. A mesogenic compound having the formula:

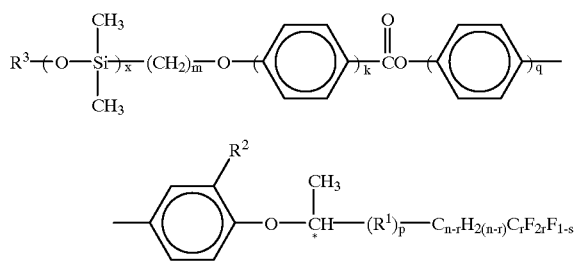

wherein $R^1$ is an ester group, $R^2$ is H, $NO_2$, CN, F, or Cl, $R^3$ is $(CH_3)_3Si$, k is 1 or 2, q is 0 or 1, m is from 2 to 16, n is from 2 to 12, p is 0 or 1, r is from 0 to 4 s=1 when r=0, s=0 when r≠0, x is from 0 to 4, and * denotes the position of a chiral carbon.

13. A mesogenic compound having the formula:

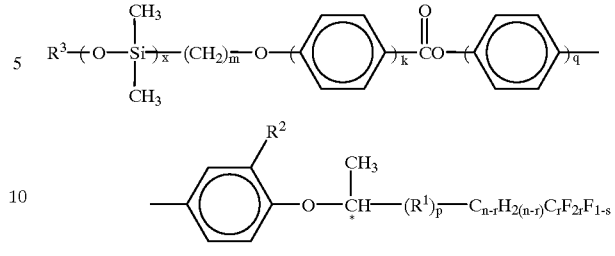

wherein $R^1$ is an ester group, $R^2$ is H, $NO_2$, CN, F, or Cl, $R^3$ is H, $CH_2=CH$, or $(CH_3)_3Si$, k is 1 or 2, q is 0 or 1, m is from 2 to 16, n is from 2 to 12, p is 0 or 1, when x=0, r=0 to 4, when x=0, r=1 to 4 s=0, x is from 0 to 4, and * denotes the position of a chiral carbon.

* * * * *